United States Patent [19]

Rauleder et al.

[11] 4,146,544

[45] Mar. 27, 1979

[54] PROCESS FOR THE PREPARATION OF (1-CHLOROETHENYL-) OXIRANE

[75] Inventors: Gebhard Rauleder, Duesseldorf; Helmut Waldmann, Leverkusen; Gerhard Scharfe, Leverkusen; Rupert Wenzel, Leverkusen, all of Fed. Rep. of Germany

[73] Assignee: Bayer Aktiengesellschaft, Leverkusen, Fed. Rep. of Germany

[21] Appl. No.: 895,578

[22] Filed: Apr. 12, 1978

[30] Foreign Application Priority Data

Apr. 21, 1977 [DE] Fed. Rep. of Germany ....... 2717673

[51] Int. Cl.$^2$ ........................................... C07D 301/00
[52] U.S. Cl. .............................................. 260/348.12
[58] Field of Search ................................... 260/348.12

[56] References Cited

U.S. PATENT DOCUMENTS 2,907,774  10/1959  MacPeek ..................... 260/348.12

FOREIGN PATENT DOCUMENTS 864882  4/1961  United Kingdom.

*Primary Examiner*—Norma S. Milestone
*Attorney, Agent, or Firm*—Sprung, Felfe, Horn, Lynch & Kramer

[57] ABSTRACT

An improved process has been invented for the production of (1-chloroethenyl)-oxirane which comprises dehydrochlorinating (1,2-dichloroethyl)-oxirane with a solution of the sodium salt of an alcohol having at least 5 carbon atoms in said alcohol and separating the (1-chloro-ethenyl)-oxirane from the reaction mixture.

13 Claims, No Drawings

PROCESS FOR THE PREPARATION OF (1-CHLOROETHENYL-) OXIRANE

The present invention relates to a process for the preparation of (1-chloroethenyl-) oxiran by dehydrochlorination of (1,2-dichloroethyl-) oxirane.

(1-chloroethenyl-) oxirane is employed for the preparation of polymers and as an organic intermediate. Up until now it has not been used on a large scale in industry since no satisfactory industrial process has yet been available for its preparation.

Several proposals have already been made for the preparation of (1-chloroethenyl-) oxirane. For example, Petrov reported in 1939 on the preparation of (1-chloroethenyl-) oxirane by the reaction of 2-chloro-1,3-butadiene with hypobromous acid and subsequent dehydrochlorination with potassium hydroxide (A. A. Petrov, J. Gen. Chem. 9,2232-43 (1939)):

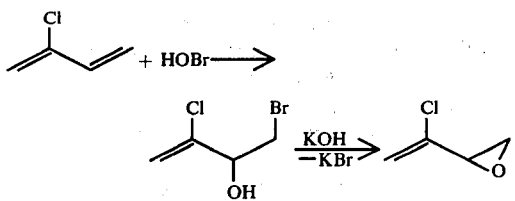

Yields were not stated. However, industrial application of this method cannot be considered because of the high cost of the hypobromous acid and the use of relatively expensive potassium hydroxide. Also a high percentage of secondary products are to expected, since it is unlikely that the hypobromous acid solely attacks the unsubstituted double bond.

In 1952 Petrov employed hypochlorous acid instead of the hypobromous acid (A. A. Petrov. J. Gen. Chem. 22,1516-28 (1952)):

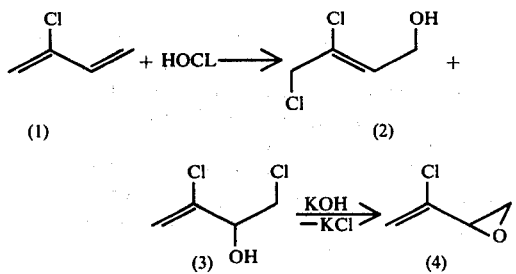

Here the hypochlorous acid even attacked to a considerable degree the double bond substituted by chlorine, i.e. the chlorohydrin (3), which is converted into (1-chloroethenyl-) oxirane (4) by dehydrochlorination, was formed in a lower proportion. The desired product is thus obtained in only a low yield, which excludes industrial application of this method.

Better yields were obtained with a method of synthesis which was published in 1957 in two patent specifications U.S. Pat. No. 2,907,774 and Brit. Pat. No. 864,882). In both of these (1,2-dichloroethyl-) oxirane is converted to (1-chlorethenyl-) oxirane with alkali hydroxide:

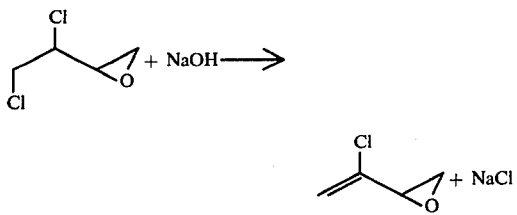

In U.S. Pat. No. 2,907,724 the dehydrochlorination is conducted with a suspension of alkali hydroxide in dialkyl ether or with a cyclic ether.

According to Example 1, column 4, line 60 et seq. potassium hydroxide is used as a suspension in diethylether for the dehydrochlorination. The yield of (1-chloroethenyl-) oxirane obtained was however only 28.7%. According to Example 2, column 5, line 20 et seq. of this USA patent specification the dehydrochlorination of (1,2-dichloroethyl-)oxirane is carried out with a suspension of sodium hydroxide in diethyleneglycol diethyl ether. The yield obtained in this was approx. 82%. The yields obtained are unsatisfactory for industrial application of this process. A particular industrial disadvantage is caused by the removal and recovery of the alkali hydroxide which is used in excess and which has to be filtered off as a precipitate together with the alkali chloride forming during the reaction.

In the Brit. Pat. No. 864,882 the dehydrochlorination of (1,2-dichloroethyl-) oxirane is conducted with aqueous alkali hydroxide in the presence of solvents such as alcohols, dioxane or ethylene glycol. According to example 3, page 2, line 80 et seq., (1,2-dichloroethyl-) oxirane is dehydrochlorinated with aqueous sodium hydroxide in the presence of methanol. The yield obtained was however, only 47.5%. Also, the use of aqueous sodium hydroxide in the presence of dioxane only produced a yield of 42% of (1-chloroethenyl-) oxirane. (Example 4, page 2, line 90 et seq. of the Brit. Pat. No. 864,882). In addition to the low yield a further disadvantage of this process is the technically complex working up procedure. Thus, according to the examples mentioned, when the reaction is completed the reaction mixture is diluted with water, extracted with an organic solvent and the organic phase is subsequently fractionated. The recovery of that amount of the solvent used during the reaction (such as methanol, dioxane or ethylene glycol which has remained in the aqueous phase, is technically very complex.

When the dehydrochlorination was conducted with aqueous sodium hydroxide alone without the addition of an organic solvent, the yield of (1-chloroethenyl)oxirane was only 36.8% (Example 6, page 2, line 110 et seq. of the Brit. Pat. No. 864,882).

The use of melted sodium hydroxide for the dehydrochlorination of (1,2-dichloroethyl-) oxirane is described in Example 9, page 3, line 18 et seq. of the Brit. Pat. No. 864,882). Despite the reintroduction into the reaction of the non-converted (1,2-dichloroethyl-) oxirane, it was only possible to increase the yield to 84% which is unsatisfactory for an industrial process. What is particularly disadvantageous for industrial application of this method is however the costly regulation of the reaction required by the use of wetted sodium hydroxide at 200° C. and the conversion rate, which at 80%-as take from example 8, page 3, line 5 et seq. of the patent specification — is completely unsatisfactory for industrial application.

Contrary to this, it has now been found that (1-chloroethenyl-) oxirane can be produced in higher yields and with a high degree of purity by dehydrochlorination of (1,2-dichloroethyl-) oxirane, if (1,2-dichloroethyl-) oxirane is reacted with a solution of the sodium salt of an alcohol with at least 5 carbon atoms of the formula

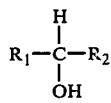

wherein $R_1$ and $R_2$, independently of each other, represent hydrogen, $C_1$- to $C_7$-alkyl, $C_5$- to $C_7$-cycloalkyl or phenyl, the sum of the carbon atoms of the radicals $R_1$ and $R_2$ being 4–14, in this alcohol at 0 to 100° C. and the (1-chloroethenyl-)oxirane is separated from the reaction mixture by distillation.

In particular the following may be mentioned as alcohols of the general formula (I): n-pentanol-(1), 2-methyl-1-butanol, 3-methyl-1-butanol, 4-methyl-2-pentanol, n-pentanol-(2), n-pentanol-(3), n-hexanol-(1), n-hexanol-(2), n-hexanol-(3), 2-methyl-1-pentanol, 3-methyl-1-pentanol, 4-methyl-1-pentanol, 2-ethyl-1-butanol,n-heptanol-(1), n-heptanol-(2), benzyl alcohol, n-octanol-(1), n-octanol-(2), 2-ethyl-1-hexanol.

Included in the compounds of formula (I) are, for example, alcohols with at least 5 carbon atoms of the formula

wherein $R_3$ represents a $C_4$- to $C_7$-alkyl radical or a phenyl radical.

In particular, the following may be mentioned as examples: n-pentanol-(1), 2-methyl-1-butanol, 3-methyl-1-butanol, n-hexanol.(1), 4-methyl-1-pentanol, 2-methyl-1-pentanol, 3-methyl-1-pentanol, n-heptanol-(1) n-octanol-(1), 2-ethyl-1-hexanol and benzyl alcohol.

n-pentanol-(1), 3-methyl-1-butanol, n-hexanol-(1), 4-methyl-2-pentanol, 2-ethyl-1-hexanol are particularly suitable for the conversion of (1,2-dichloroethyl-) oxirane according to the process of the invention. n-pentanol-(1), n-hexanol-1 and 2-ethyl-1-hexanol are most particularly suitable for the dehydrochlorination of (1,2-dichloroethyl-)oxirane according to the process of invention.

Apart from using one of the above-mentioned alcohols of the general formula I one can also use the sodium salt of a mixture of two or more of the above-mentioned alcohols for the dehydrochlorination of (1,2-dichloroethyl-)oxirane.

The preparation of the solution of the sodium alcoholate in the corresponding alcohol is advantageously conducted by azeotropic dehydration of, for example, 50% strength sodium hydroxide solution with the alcohol corresponding to the required sodium alcoholate. By this procedure an essentially anhydrous solution of the sodium alcoholate in the corresponding alcohol is obtained.

The concentration of the sodium alcoholate in the corresponding alcohol can vary within wide limits. For example, sodium alcoholate concentrations of appr. 0.1% by weight to appr. 50% by weight, i.e. up to the range of supersaturation, can be used; the saturation concentration of the sodium alcoholate in the corresponding alcohol can however be different for different alcohols. Suitable sodium alcoholate concentrations are those whose concentrations are appr. 1 to 30% by weight in the corresponding alcohol. Particularly prefereable are solutions with a concentration of appr. 5 to 25% by weight sodium alcoholate. Most particularly preferable for the dehydrochlorination of (1,2-dichloroethyl-)oxirane are sodium alcoholate solutions with a concentration of appr. 10 to 20% by weight. In special cases the concentrations mentioned can be higher or lower.

The reaction of this solution of sodium alcoholate in alcohol with (1,2-dichloroethyl-)oxirane occurs in the liquid phase at temperatures of 0 to 100° C. The reaction is preferably conducted at 20 to 80° C., especially at 40 to 60° C. Also, in special cases the reaction can take place below or above the temperatures stated.

Apart from conducting the process under isothermal conditions, i.e. maintaining a uniform temperature in the whole reaction mixture, the reaction can also be conducted by the formation of a so-called temperature gradient which, in general, increases as the reaction progresses. One can however regulate the reaction in such a way that as the reaction progresses a gradient of decreasing temperature is formed.

The molar ratio of sodium alcoholate to (1,2-dichloroethyl-)oxirane can vary within wide limits. It can for example be 1:2 to 2:1. In a preferred embodiment of the process a molar ratio of 1.0:1.0 to 1.1, or 1.0 to 1.1:1.0, e.g. 1:1 of sodium alcoholate to (1.2-dichloroethyl-)oxirane can be employed. With a ratio of sodium alcoholate to (1.2-dichloroethyl-)oxiration of 1.0:1.0 to 1.1 a practically complete conversion of the sodium alcoholate can be achieved, so that the resulting reaction mixture is practically free from sodium alcoholate. With a ratio of 1.0 to 1.1 : 1.0 of sodium alcoholate to (1,2-dichloroethyl-)oxirane a practically complete conversion of the (1,2-dichloroethyl-) oxirane can take place, so that the reaction mixture is practically free from (1,2-dichloroethyl-)oxirane.

The process according to the invention can be conducted at various pressures. In general it is conducted at normal pressure; the process can however also be conducted under reduced or under excess pressure.

The water content of the solution of sodium alcoholate in alcohol used for the dehydrochlorination should in general be as low as possible. Low quantities of water, up to 1% by weight do not in general interfere with the reaction. Preferably a sodium alcoholate solution is employed which contains less than 0.3% by weight of water. A water content of less than 0.1% by weight is particularly preferred.

The dehydrochlorination can be conducted either discontinuously or continuously in the customary devices for reactions of this kind, such as stirrer vessels, boiling reactors, tube reactors, loop reactors of different designs.

The reaction heat is removed by internally or externally arranged coolers. For the removal of the reaction heat the reaction can also be conducted under reflux (boiling reactors).

In an industrial embodiment of the process (1,2-dichloroethyl-)oxirane is reacted with sodium alcoholate at a molar ratio of 1.0 to 1.1:1.0. In this a quantitative conversion of sodium alcoholate is obtained, the reaction mixture possibly still containing small quantities of non-converted (1,2-dichloroethyl-)oxirane. The sodium chloride produced in the dehydrochlorination is to a large extent anhydrous and occurs in finely-grained solid form as a suspension in the reaction mixture. The distillative separation of the (1-chloroethenyl-)oxirane can take place immediately upon completion of the dehydrochlorination, various working up processes being able to be selected. It is possible, for example, to remove the sodium chloride mechanically from the reaction mixture, e.g. by filtration or centrifuging before the distillative separation of the (1-chloroethenyl-)oxirane and, following this, isolate (1-chloroethenyl-)oxirane in pure form from the sodiumchloride-free solution, by means of distillation. It is however also possible to introduce the reaction mixture into a distillation column without previously separating the sodium chloride, pure (1-chloroethenyl-)oxirane being obtained as the top product and as the sump product a suspension of sodium chloride in alcohol which possibly contains small quantities of (1,2-dichloroethyl-)oxirane. Sodium chloride is then able to be mechanically separated from the sump product. In a further embodiment of the process the distillative separation of the (1-chloroethenyl-)oxirane oxirane takes place by conducting the dehydrochlorination in a cascade of stirrer vessels with attached distillation columns, ((1-chloroethenyl)-oxirane being obtained as the top product and a sump product free from (1-chloroethenyl-)oxirane. From the sump product the sodium chloride is able to be separated again mechanically.

The mechanical speparation of the sodium chloride can for example be conducted in a dry thin film evaporator. In this way it is possible to obtain sodium chloride free from alcohol and oxirane.

The alcohol can, following the separation of (1,2-dichloroethyl-)oxirane be reintroduced into the stage for the preparation of the solution of the sodium alcoholate in the corresponding alcohol by azeotropic dehydration of sodium hydroxide solution. By the recovery of the alcohol and the reintroduction into the azeotropic dehydration no alcohol is required as the raw material for the production of (1-chloroethenyl-) oxirane. The raw materials required for the process are sodium hydroxide and (1,2-dichloroethyl-) oxirane. The total reaction can be illustrated by the equation (1,2-dichloroethyl-)oxirane + NaOH→ (1-chloroethenyl-)oxirane + NaCl + H$_2$O. An essential characteristic of the process is that the water produced in the reaction preceding dehydrochlorination can be obtained in the form of a clear effluent and that the sodium chloride is obtained in solid, anhydrous form.

The following examples illustrate the invention. All the percentages represent, unless otherwise stated, percentages by weight.

EXAMPLE 1

By azeotropic dehydration of 50% strength sodium hydroxide solution with n-pentanol-1 a substantially anhydrous 20-25% strength solution of sodium pentylate in n-pentanol-1 (with a water content of $\leq 0.1\%$) is obtained.

282 g (2mols) of (1,2-dichloroethyl-)oxirane were placed in a 2 l-three-necked flask with reflux cooler, KPG-stirrer and dropping funnel and heated to 40° C. With vigorous stirring 956.5 g of a 23% strength sodium pentylate solution in n-pentanol-1 were added dropwise within one hour, an inner temperature of approx. 54° C. forming in the reaction flask. Following the dropwise addition of the above stirring was continued for a further half an hour at this temperature, then the titrimetric analysis showed that the sodium pentylate conversion was over 99%. The gas chromatographic analysis showed a selectivity of 96% for (1-choroethenyl)oxirane.

The fractionation of this reaction mixture, which contained in suspension the sodium chloride obtained, with a 30 cm packed column and at a pressure of 50 mm Hg produced (1-choroethenyl-)oxirane at a yield of 192.3 g (92%) and a purity of over 99%.

EXAMPLE 2

The dehydrochlorination of (1,2-dichloroethyl-)oxirane with 23% strength sodium pentylate in n-pentanol-1 was conducted as described in example 1. After the reaction was completed the reaction mixture of the sodium chloride which was produced in easily filterable form was separated off by filtration.

The subsequent fractionation of the filtrate produced (1-chloroethenyl-)oxirane in a yield of 94.6% and of a purity of over 99%.

EXAMPLE 3

423 g (3 mols) of (1,2-dichloroethyl-)oxirane were placed in a 2 l-three-necked flask with dropping funnel, KPG-stirrer and distillation attachment (30 cm packed column) and heated to 54° C. With a vacuum of 15 mm Hg, 1434.8 g of 23% strength sodium pentylate solution in n-pentanol-1 were added dropwise under vigorous stirring and the (1-chloroethenyl-) oxirane was distilled off continuously. After the reaction was completed 294.7 g of (1-chloroethenyl-)oxirane were obtained; this corresponds to a yield of 94%.

EXAMPLE 4

By azeotropic dehydration of 50% strength sodium hydroxide solution with n-hexanol-1 a substantially anhydrous 22% strength solution of the sodium salt of n-hexanol-1 in n-hexanol-1 was obtained. 282 g (2 mols) of (1,2-dichloroethyl-)oxirane were reacted with 2 mols of this 22% strength solution of the sodium salt of n-hexanol-1 in n-hexanol as described under example 1. The titrimetric analysis showed, after the reaction was completed, a 99% conversion and the gas chromatographic analysis showed that (1-chloroethenyl-)oxirane was produced in a selectivity of 95.8%. Following fractionation of the reaction mixture at 50 mm Hg (1-chloroethenyl-)oxirane was obtained in a yield of 93%.

EXAMPLE 5

The process was conducted as in Example 1: instead of n-pentanol-1, however, 2-ethyl-1-hexanol was employed. After fractionating the reaction mixture at 50 mm Hg (1-chloro-ethenyl-) oxirane was obtained in a yield of 92%.

EXAMPLE 6

By azeotropic dehydration of 50% strength sodium hydroxide solution with n-hexanol-1 a 15% strength solution of sodium hexylate in n-hexanol-1 was obtained. The dehydrochlorination of (1,2-dichloroethyl-)oxirane oxirane with the sodium hexylate solution prepared as above was conducted as described in Example 1.

Following fractionation of the reaction mixture (1-chloroethenyl-)oxirane was obtained in a yield of 93.1%.

EXAMPLE 7

By azeotropic dehydration of 50% strength sodium hydroxide solution with a mixture of 50% by weight of npentanol-1 and 50% by weight of n-hexanol-1 a substantially anhydrous 17.5% strength solution of the sodium salts of n-pentanol-1 and n-hexanol-1 in a mixture of n-pentanol-1 and n-hexanol-1 was obtained. The dehydrochlorination of (1,2-dichloroethyl-)oxirane with the sodium alcoholate solution thus prepared was conducted as described in Example 1. Following fractionation of the reaction mixture (1-dhloroethenyl-)oxirane was obtained in a yield of 93%.

EXAMPLE 8

(1,2-dichloroethyl-)oxirane was reacted with a 10% strength solution of sodium pentylate in n-pentanol-1 at a molar ratio of 1.03 of sodium pentylate to (1,2-dichloroethyl-)oxirane and at an average residence time of 2.5 hours in a four-step cascade of glass vessels, distillation columns being connected to the cascade. The cascade was operated at a vacuum of 50 millibars.

According to this method (1,2-dichloroethyl-)oxirane was practically completely converted and (1-chloroethenyl-)oxirane was obtained as top product having over 99% purity and in a yield of 93.5%. The reaction temperature in the first first vessel was appr. 55° C.; it was increased from vessel to vessel to such a degree that the last vessel was practically free from (1-chloroethenyl-)oxirane.

The common salt was filtered off from the sump product, which consisted practically exclusively of n-pentanol-1 and sodium chloride; n-pentanol-1 was reintroduced, following redistillation, into the step for the preparation of the sodium pentylate.

What is claimed is:

1. A process for the preparation of (1-chloroethenyl-)oxirane by dehydrochlorination of (1,2-dichloroethyl-)oxirane which comprises reacting (1,2-dichloroethyl-)oxirane with a solution of the sodium salt of an alcohol with at least 5 carbon atoms of the formula

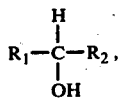

wherein $R_1$ and $R_2$, independently of each other, denote hydrogen, $C_1$ to $C_7$ alkyl, $C_5$ to $C_7$ cycloalkyl or phenyl, the sum of the carbon atoms of the radicals $R_1$ and $R_2$ being 4–14, in this alcohol at 0° to 100° C. and separating (1-chloroethenyl-)oxirane from the reaction mixture by distillation.

2. A process according to claim 1, wherein the sodium salt of an alcohol of the formula $$, R_3-CH_2-OH,$$

wherein $R_3$, represents a $C_4$ to $C_7$ alkyl radical or a phenyl radical, is used.

3. A process according to claim 1 wherein the sodium salt of n-pentanol-1 is used.

4. A process according to claim 1 wherein the sodium salt of iso-amyl alcohol is used.

5. A process according to claim 1 wherein the sodium salt of 4-methyl-2-pentanol is used.

6. A process according to claim 1 wherein the sodium salt of 2-ethyl-1-hexanol is used.

7. A process according to claim 1 wherein the sodium salt of n-hexanol-1 is used.

8. A process according to claim 1 wherein the process is conducted with a water content in the solution of the sodium salt of an alcohol in this alcohol of less than 1% by weight.

9. A process according to claim 1 wherein a solution of the sodium salt of the alcohol in the alcohol is used which solution has been prepared by azeotropic dehydration of aqueous sodium hydroxide solution with the alcohol.

10. A process according to claim 1 wherein the dehydrochlorination is conducted with a molar ratio of sodium alcoholate to (1,2-dichloroethyl-)oxirane of 1.0:1.0 to 1.1 or 1.0 to 1.1:1.0.

11. A process according to claim 1 wherein the alcohol is completely or partially separated from the reaction mixture and is reintroduced into the stage for the preparation of the solution of the sodium salt of an alcohol in this alcohol.

12. A process according to claim 1 wherein the reaction mixture obtained is introduced into a distillation column and is separated into (1-chloroethenyl-)oxirane as top product and a sump product containing sodium chloride and free from (1-chloroethenyl-)oxirane.

13. A process according to claim 1 wherein the reaction of the solution of the sodium salt of an alcohol in this alcohol with (1,2-dichloroethyl-)oxirane is conducted in a reaction unit under vacuum and the reaction product in vapour state is introduced into a distillation column and separated into (1-chloroethenyl-)oxirane as top product and a sump product which contains the alcohol corresponding to the sodium alcoholate used and possibly (1,2-dichloroethyl)oxirane, and this sump product is reintroduced into the reaction unit.

* * * * *